United States Patent [19]

Hansen

[11] Patent Number: 4,465,571

[45] Date of Patent: Aug. 14, 1984

[54] THIODIPROPIONOYL BIS(HALO 5-NORBORNENE 2,3-DICARBOXYLIC ACID HYDRAZIDE) ADDITIVES FOR POLYMERS

[75] Inventor: Ralph H. Hansen, Lincoln, Mass.

[73] Assignee: Canusa Coating Systems Limited, Ontario, Canada

[21] Appl. No.: 439,865

[22] Filed: Nov. 8, 1982

[51] Int. Cl.$^3$ ............... C07D 209/94; C08K 5/34
[52] U.S. Cl. ............................................. 204/159.2
[58] Field of Search ................. 524/89; 548/435; 204/159.2; 174/110

[56] References Cited

U.S. PATENT DOCUMENTS

| | | | |
|---|---|---|---|
| T861,006 | 4/1969 | Tholstrup | 524/192 |
| 3,061,642 | 10/1962 | Weisse et al. | 564/136 |
| 3,364,217 | 1/1968 | Cyba | 524/89 |
| 3,455,950 | 7/1969 | Cyba et al. | 524/89 |
| 4,026,963 | 5/1977 | Rim et al. | 548/435 |
| 4,087,405 | 5/1978 | Wang et al. | 524/192 |
| 4,178,280 | 12/1979 | Hill | 548/435 |
| 4,189,423 | 2/1980 | Kumano et al. | 524/94 |

FOREIGN PATENT DOCUMENTS 64337 11/1973 Japan.
1287934 9/1968 United Kingdom.

*Primary Examiner*—Veronica P. Hoke
*Attorney, Agent, or Firm*—Sewall P. Bronstein; Donald Brown

[57] ABSTRACT

A compound of the formula (I)

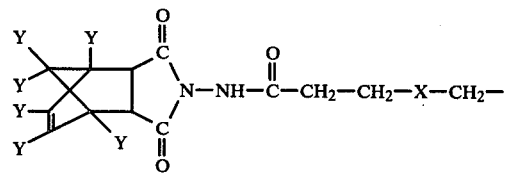

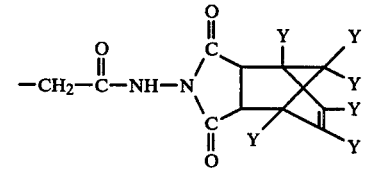

Polymer compositions including antioxidants and the compounds or the compound alone are useful as electrical insulation e.g., for copper cable, as heat shrinkable (heat recoverable) parts or as other plastic parts to improve the retention of mechanical and/or electrical properties of the insulation or parts.

18 Claims, 7 Drawing Figures

THIODIPROPIONOYL BIS(HALO 5-NORBORNENE 2,3-DICARBOXYLIC ACID HYDRAZIDE) ADDITIVES FOR POLYMERS

BRIEF STATEMENT OF THE INVENTION

This invention is directed to compounds of the formula (I)

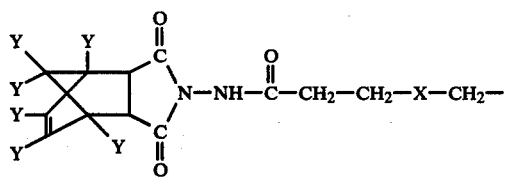

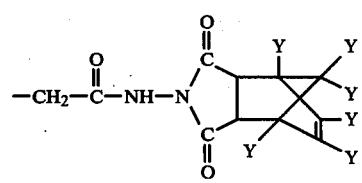

where Y is Cl or Br and is preferably C, X is S or S-S, and is preferably S, and its use in polymers as a flame retardant and as a synergist for antioxidants used in such polymers as well as an antioxidant in its own right, and articles of manufacture comprising polymers with the compounds.

While it would be expected that the compounds (I) would have nil antioxidant properties at elevated temperatures in a polymer unexpectedly the compounds of formula (I) have antioxidant properties comparable to compounds which would be considered to be primary antioxidants. The compound will also, when used in combination with one or more primary antioxidants, substantially and unexpectedly increase the useful life of the polymer at elevated temperatures without requiring the high loading of the primary antioxidants (also referred to as chain breaking antioxidants).

While it may be possible to use additional antioxidants, to achieve the increased polymer life at elevated temperatures, primary antioxidants commonly used tend to diffuse out of the polymer at high concentrations and form undesirable coating (termed blooming) on the surface thereof. In addition, the loss of primary antioxidant will over a period of time permit oxidation to take place at an accelerated rate and thereby significantly decrease the mechanical and electrical properties of the polymer thus shortening its lifetime. The commonly used antioxidant synergist (synergists are sometimes referred to as secondary antioxidants, and also referred to as peroxide decomposing antioxidants) DLTDP (dilauryl thiodipropionate) also is known to bloom.

The present invention is useful in polymers used for electrical insulation, in heat shrinkable tubing and other parts, e.g., end caps made of polyethylene and used for electrical purposes, as well as in other plastic (polymer) parts used as utensils or as parts of the tubs of washing machines to prevent them from becoming brittle due to loss of antioxidant (because of soapy water causing the antioxidants commonly used to leach out of the plastic).

The compounds of formula (I) are particularly useful in heat recoverable (heat shrinkable) articles of manufacture such as tubing, end caps, boots and other hollow articles to which heat is applied to cause shrinkage because the lack of blooming permits coating with adhesives which may contain metal particles.

Polymers in which the compounds of formula (I) are useful in this invention include all thermoplastics and thermohardening (thermosetting) plastics in which antioxidants are employed. Suitable plastics may include polyolefins such as polyethylene (high and low density), polypropylene, polybutylene, substituted polyolefins such as halogenated olefin polymers and copolymers of same and silane grafted polyethylenes, e.g., grafted using a silane such as vinyl trimethoxy silane as the grafting agents, (see U.S. Pat. No. 3,086,242).

The compounds of formula (I) would also be useful with any polymer whose useful properties are adversely affected by oxidative degradation such as esters, amides (e.g., nylon), phenolics, acrylics, rubber, urethanes, vinyls, styrenes (e.g. ABS), and others used in the plastics industry. See the Text PLASTICS IN THE MODERN WORLD by E. G. Couzens and V. E. Yarsly © 1968, published by Pelican Books, Inc., Maryland U.S.A., for other polymers used in industry and useful in this invention.

Prior art patents showing heat recoverable plastics and articles include U.S. Pat. Nos. 4,048,129, 4,106,356, 3,981,546 and 3,959,052. It should be understood that heat recoverable articles are meant to include those that are treated by irradiation or chemically treated to produce such articles.

Examples of primary antioxidants useful in a polymer with the compound of formula (I) include:

| ANTIOXIDANTS | |
|---|---|
| Commercial Name | Chemical Name |
| Irganox 1010 | tetrakis[methylene-3(3',5'-di-tert-butyl-4'-hydroxyphenyl)propionate]methane |
| Santonx R | 4,4'-thiobis(3-methyl-6-tert-butyl phenol) |
| Irganox 1024 | N,N'—bis(3,5-di-tert-butyl-4-hydroxy-hydrocinnamoyl)hydrazine |
| Cyanox 1729 | Bis(4-tert-butyl-3 hydroxy-2,6-dimethyl benzyl) dithiolterephthalate |
| Ethyl 330 | 1,3,5,Trimethyl-2,4,6-tris[3,5 di-tert-butyl- 4 hydroxy benzyl]-benzene |
| Agerite White | di-β-naphthyl-p-phenylene-diamine |
| Irganox 1035 | thiodiethylene bis(3,5-di-tert-butyl-4-hydroxy) hydrocinnamate |

Other suitable commercial antioxidants include Good-Rite 3114, Plastanox 2246, Naugard 449, Naugard XL-1, Irganox 1093, Irganox 1076, Topanol CA, and Iraganox 565. Other antioxidants (normally termed primary antioxidants) in the art may be found in the test ANTIOXIDANTS, RECENT DEVELOPMENTS, CHEMICAL TECHNOLOGY REVIEW NO. 127, by M. William Ronney, Noyes Data Corporation (C) 1979, Library of Congress, Catalog No. 79-84425.

In using this invention to form polymeric articles, when the compounds of formula (I) are used as antioxidant synergistics, it is preferred that an amount of the compound of formula (I) to the amount of antioxidant is in the ratio of 1:10 to 10:1 with the total weight of antioxidant and the compounds of formula (I) being within the range of 0.05 to 10% based on the weight of the polymer (resin) and at concentrations as high as 150% of the weight of the polymer in a fire resistant composition for their flame retardant properties.

The compounds of formula (I) provide the sulfur for synergism with primary (strong) antioxidants (see list of antioxidants on previous page).

In using the compound of formula (I) by itself in a polymer the concentration used should preferably be between 0.05 to 10% of the weight of the polymer when used as an antioxidant and at concentrations as high as 150% (generally 50 to 100%) of the weight of the polymer for a fire resistant composition.

In FIGS. 1 to 7 there are shown various forms of the invention. FIGS. 1 to 5 illustrate hollow articles as does FIG. 7.

FIGS. 1, 2 and 3 illustrate a tube 20 formed of material such as vinyl trimethoxysilane grafted polyethylene and containing an antioxidant and a compound of formula (I) or a compound of formula (I) alone.

The tube is formed by conventional technology to be heat shrinkable e.g., see U.S. Pat. Nos. 3,086,242 and 3,303,243. See U.K. Patent Application No. 1601063 published Oct. 21, 1981 for an illustration of chemically produced heat shrinkable material. Conventional crosslinked silane grafted polyethylene is shown in U.S. Pat. No. 3,086,242. The material of U.S. Pat. No. 3,086,242 will be modified by the incorporation of antioxidant and the compound of formula (I) as disclosed herein.

The tube 20 is shrunk as shown in FIG. 3 over electrical cable 21 to provide an insulative protective cover which will protect against moisture and other deleterious substances.

FIGS. 4 and 5 illustrate a heat recoverable end cap 25 (a closed at one end hollow article) with FIG. 5 showing the end cap 25 shrunk over a pair of wires 26 and 27. The end cap 25 is made by using the polymer material of the invention in a manner well known in the art.

FIGS. 6 and 7 show a sheet 30 of material of the invention rolled over uponitself as in FIG. 7 to form a tube. The sheet may be heat recoverable or not depending upon the desires of the end use. A heat recoverable sheet may be made by methods known in the art.

In this invention, the preferred primary antioxidants are those characterized in the art as hindered phenolics or aromatic amines.

Figure 1:
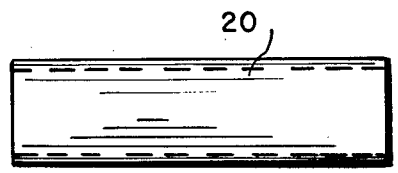
FIG. 1 is a side view of a tube.
Figure 2:
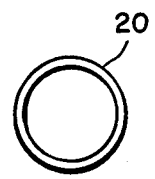
FIG. 2 is an end view of a tube.
Figure 3:
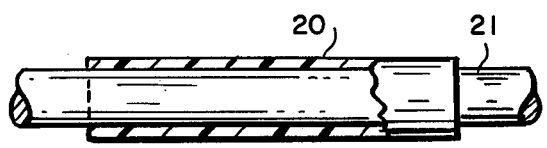
FIG. 3 is a sectional view of the tube of FIGS. 1 and 2 shrunk over wire or cable.
Figure 4:
FIG. 4 is a sectional view of an end cap.
Figure 6:
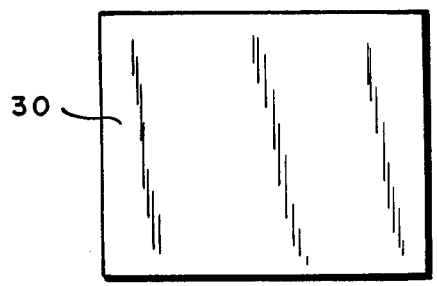
FIG. 6 is a top view of a sheet of polymer material of the invention.
Figure 5:
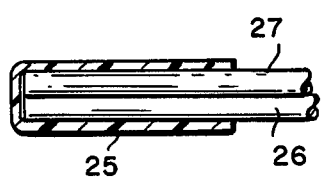
FIG. 5 is a sectional view of the end cap of FIG. 4 shrunk over a pair of wires.
Figure 7:
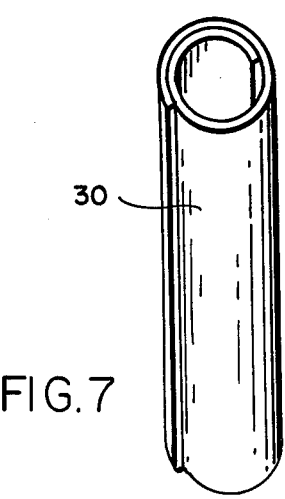
FIG. 7 is a perspective view of the sheet of FIG. 6 rolled up upon itself to form a tube.

The following examples are illustrative of the practice of the invention and are not intended for purposes of limitation. All parts are by weight and all temperatures are in centigrade.

EXAMPLE 1

Preparation of a compound of formula (I) where each Y is Cl and X is S.

The compound of formula (I) is prepared in two steps as follows: Sixty ml. of water is heated to about 60° C. and 10 grams of dimethyl thiodipropionate

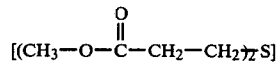

are added with stirring.

To this two-phase composition is added 7.3 grams of hydrazine hydrate [NH$_2$NH$_2$]H$_2$O (a 50% excess) while stirring is continued. In about 5 minutes the suspension clarifies and reaction appears to be complete. Stirring is continued for an additional 25 minutes and the solution is cooled to about 5° C. (crystals form at about 35° to 45° C.), filtered and dried. The yield is about 7.5 grams of thiodipropionic acid dihydrazide, m.p. 154° C. (Perkin-Elmer DSC-2 calorimeter at a heating rate of 10°/minute). The yield may be increased by re-using the mother liquor in place of the water, by concentrating the mother liquor, or by diluting with a poor solvent for the dihydrazide such as methanol.

The thiodipropionic acid hydrazide

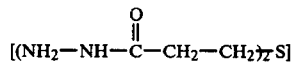

is used without further purification. To 300 ml of water at room temperature is added 8 grams of powdered 1,4,5,6,7,7-hexachloro-norborne-2,3,-dicarboxylic anhydride (chlorendic anhydride and 10 grams of the thiopropionic dihydrazide, with stirring. After approximately one hour the temperature is raised to 100° C. over a two-hour period. The material is washed with water, filtered and dried.

A nearly quantitative yield of the compound of formula (I), where each Y is Cl and X is S is obtained.

This material melts at about 280° C. (Perkin-Elmer DSC-2 calorimeter at a heating rate of 10° C. per minute). It is substantially white and is insoluble in boiling water.

EXAMPLE 2

Using the compound of formula (I) prepared in Example I, a number of compositions were prepared by mixing the proportions of ingredients (percent by weight shown) into a polymer comprising 9% vinyl acetate—91% ethylene copolymer (commercially known as U.S. Industrial Chemicals UE 635) on a heated, two-roll mill, molding into a sheet approximately 75 mils thick as shown below:

(i) 0.5 part by weight of Naugard LX-1 [2,2-oxamido bis ethyl, 3(3,5-di-tert-butyl-hydroxyphenyl) propionate] and 3 parts by weight compound of formula (I) and 100 parts by weight of the polymer;
(ii) 3 parts by weight of the compound of formula (I) and 100 parts by weight of the polymer; and
(iii) 1 part by weight of the compound of formula (I) and 100 parts by weight of the polymer; and
(iv) 0.47 part by weight of the compound of formula (I) and 100 parts by weight of an ethylene homopolymer (commercially known as U.S. Industrial Chemicals NA 254).

EXAMPLE 3

Preparation of the compound of formula (I) where each Y is Cl and X is S-S, the compound of formula (I) is prepared in two steps as follows:

Sixty ml. of water is heated to about 60° C. and 11.6 grams of dimethyl dithiodipropionate

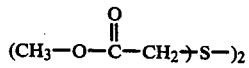

are added with stirring.

To this two-phase composition is added 7.3 grams of hydrazine hydrate [NH₂NH₂]H₂O (a 50% excess) while stirring is continued. In about 5 minutes the suspension clarifies and reaction appears to be complete. Stirring is continued for an additional 25 minutes and the solution is cooled to about 5° C. (crystals form at about 35° to 40° C.), filtered and dried. The yield is about 7.5 grams of dithiodipropionic acid dihydrazide, m.p. 270° C. (Perkin-Elmer DSC-2 calorimeter at a heating rate of 10° per minute). The yield may be increased by re-using the mother liquor in place of the water, by concentrating the mother liquor, or by diluting with a poor solvent for the dihydrazide such as methanol.

11.6 grams of the dithiodipropionic acid hydrazide

and 8 grams of powdered 1,4,5,6,7,7-hexachloro-5-norbornene-2,3-dicarboxylic anhdride are used without further purification. To 300 ml. of water at room temperature is added the 11.6 grams and 8.0 grams of of the above compound, with stirring. After approximately one hour, the temperature is raised to 100° C. over a two-hour period. The material is washed with water, filtered and dried.

A nearly quantitative yield (17 grams) of the compound of formula (I). This material is substantially white and is insoluble in boiling water.

EXAMPLE 4

Using the compound of formula (I) prepared in Example 3 a number of compositions were prepared by mixing the proportions of ingredients (percent by weight shown) into a polymer comprising 9% vinyl acetate—91% ethylene copolymer (commercially known as U.S. Industrial Chemicals UE 635) on a heated, two-roll mill, molding into a sheet approximately 75 mils thick as shown below:
(i) 0.5 part by weight of Naugard XL-1 [2,2-oxamidabis ethyl, 3(3,5-di-tert-butyl-hydroxyphenyl)propionate]; and 3 parts by weight of the compound of formula (I) and 100 parts by weight of the polymer;
(ii) 3 parts by weight of the compound of formula (I) and 100 parts by weight of the polymer;
(iii) 1 part by weight of the compound of formula (I) and 100 parts by weight of the polymer; and
(iv) 0.49 part by weight of the compund of formula (I) and 100 parts by weight of an ethylene homopolymer (commercially known as U.S. Industrial Chemicals NA 254).

I claim:
1. A compound of the formula (I)

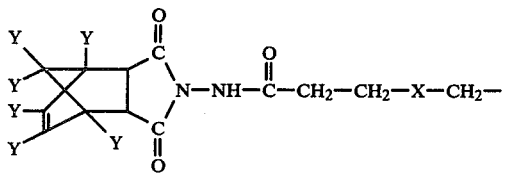

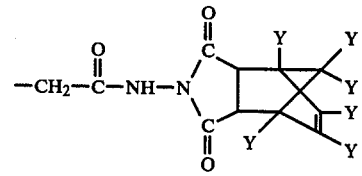

where X is S or S-S and Y is Cl or Br.
2. The compound of claim 1 in which each Y is Cl.
3. The compound of claim 1 in which each Y is Br.
4. A composition comprising a polymer and the compound of claim 1 in an amount sufficient to impart flame retardant and antioxidant properties.
5. The composition of claim 4 containing additional antioxidant.
6. As an article of manufacture, an electrical conductor and a layer of insulation about said conductor comprising the composition of claim 4.
7. The composition of claim 4 in which the polymer is polyethylene or polypropylene.
8. The composition of claim 4 in which the amount of the compound of formula (I) comprises 0.05 to 150% based on the weight of the polymer.
9. The composition of claim 5 in the form of a hollow article.
10. The composition of claim 5 in which the polymer is a polyolefin.
11. The composition of claim 5 in which the ratio of the compound of formula I to the antioxidant is 1:10 to 10:1 and the amount of the antioxidant and the compound of formula (I) is 0.05% to 10% based on the weight of the polymer.
12. The composition of claim 5 in which the additional antioxidant is a hindered phenolic or an aromatic amine.
13. The composition of claim 9 in which the hollow article is heat shrinkable.
14. As an article of manufacturer, a heat recoverable article comprising a polymer and the compound of formula (I)

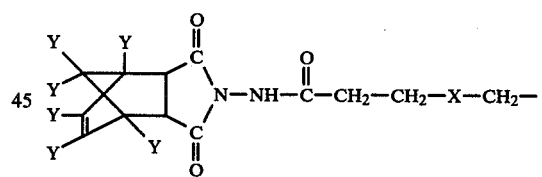

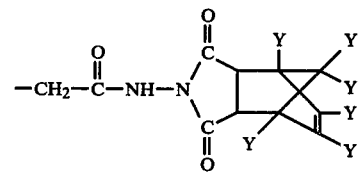

in an amount sufficient to impart flame retardant and antioxidant properties in the presence or absence of an additional antioxidant, where S is S or S-S and Y is Cl or Br.
15. The article of claim 14 in which the polymer is a polyolefin.
16. The article of claim 15 in which the polymer is polyethylene.
17. The article of claim 16 in which the polyethylene is cross-linked with silane or by irradiation.
18. The article of claim 17 in which the silane is vinyl trimethoxysilane.

* * * * *